United States Patent
Lee et al.

(10) Patent No.: US 11,091,411 B2
(45) Date of Patent: Aug. 17, 2021

(54) HYDROCRACKING CATALYST FOR PREPARING LIGHT AROMATIC HYDROCARBON, METHOD FOR PREPARING SAME AND METHOD FOR PREPARING LIGHT AROMATIC HYDROCARBON BY USING SAME

(71) Applicants: S-OIL CORPORATION, Seoul (KR); DONG-A UNIVERSITY RESEARCH FOUNDATION FOR INDUSTRY-ACADEMY COOPERATION, Busan (KR)

(72) Inventors: Jung Kyoo Lee, Busan (KR); Jaeuk Shin, Busan (KR); Yeseul Choi, Busan (KR); Soon Cheol Chang, Ulsan (KR); Heung Jung Kang, Ulsan (KR); Dong Il Kang, Ulsan (KR)

(73) Assignees: S-OIL CORPORATION, Seoul (KR); DONG-A UNIVERSITY RESEARCH FOUNDATION FOR INDUSTRY-ACADEMY COOPERATION, Busan (KR)

( * ) Notice: Subject to any disclaimer, the term of this patent is extended or adjusted under 35 U.S.C. 154(b) by 0 days.

(21) Appl. No.: 16/345,085

(22) PCT Filed: Oct. 27, 2016

(86) PCT No.: PCT/KR2016/012151
§ 371 (c)(1),
(2) Date: Apr. 25, 2019

(87) PCT Pub. No.: WO2018/079876
PCT Pub. Date: May 3, 2018

(65) Prior Publication Data
US 2019/0284111 A1    Sep. 19, 2019

(30) Foreign Application Priority Data

Oct. 26, 2016    (KR) ........................ 10-2016-0140129

(51) Int. Cl.
*C07C 4/18*       (2006.01)
*B01J 29/46*      (2006.01)
(Continued)

(52) U.S. Cl.
CPC ................. *C07C 4/18* (2013.01); *B01J 29/46* (2013.01); *B01J 29/48* (2013.01); *B01J 29/72* (2013.01);
(Continued)

(58) Field of Classification Search
CPC ... C07C 4/18; C07C 2529/46; C07C 2529/48; C07C 2529/76; C07C 2529/78;
(Continued)

(56) References Cited

U.S. PATENT DOCUMENTS

2003/0019792 A1*  1/2003  Chen .................... C10G 35/065
                                                               208/134
2009/0314683 A1* 12/2009  Matsushita ............ C10G 47/12
                                                               208/111.3
(Continued)

FOREIGN PATENT DOCUMENTS

EP       1640434        3/2006
EP       1640434 A1 *   3/2006    ........... C10G 49/002
(Continued)

*Primary Examiner* — Youngsul Jeong
*Assistant Examiner* — Jason Y Chong
(74) *Attorney, Agent, or Firm* — Duane Morris LLP; Gregory M. Lefkowitz (57) ABSTRACT

The present disclosure relates to a hydrocracking catalyst for preparing a $C_6$-$C_9$ light aromatic hydrocarbons having an increased BTX content from a polycyclic aromatic hydrocarbon, a method for preparing the same and a method for preparing a $C_6$-$C_9$ light aromatic hydrocarbons having an (Continued)

US 11,091,411 B2

Page 2 increased BTX content by using the same. More specifically, an effect of obtaining a $C_6$-$C_9$ light aromatic hydrocarbons having an increased BTX content with a high yield from the byproducts of oil refining and petrochemical processes, which contain polycyclic aromatic hydrocarbons such as naphthalene, alkylnaphthalene, etc., can be achieved by using a catalyst in which one or more metal selected from group VIII and one or more metal selected from group VIB are supported on a composite zeolite support of zeolite beta and zeolite ZSM-5.

12 Claims, 2 Drawing Sheets (51) Int. Cl.
*B01J 29/48* (2006.01)
*B01J 29/76* (2006.01)
*B01J 29/78* (2006.01)
*B01J 29/80* (2006.01)
*B01J 37/02* (2006.01)
*B01J 37/08* (2006.01)
*B01J 29/72* (2006.01)
*B01J 37/00* (2006.01)

(52) U.S. Cl.
CPC ........... *B01J 29/7615* (2013.01); *B01J 29/78* (2013.01); *B01J 29/7815* (2013.01); *B01J 29/80* (2013.01); *B01J 37/00* (2013.01); *B01J 37/02* (2013.01); *B01J 37/0201* (2013.01); *B01J 37/08* (2013.01); *C07C 2529/46* (2013.01); *C07C 2529/48* (2013.01); *C07C 2529/76* (2013.01); *C07C 2529/78* (2013.01); *C07C 2529/80* (2013.01)

(58) Field of Classification Search
CPC ....... C07C 2529/80; B01J 29/24; B01J 29/26; B01J 29/40; B01J 29/46; B01J 29/48; B01J 29/7007; B01J 29/72; B01J 29/7615; B01J 29/78; B01J 29/7815; B01J 29/80; B01J 37/00; B01J 37/02; B01J 37/0201; B01J 37/08; B01J 37/20; B01J 23/882; B01J 23/883; B01J 35/0006; B01J 27/047; B01J 23/85; B01J 23/88; B01J 21/12; C10G 2400/30; C10G 11/02

See application file for complete search history.

(56) References Cited

U.S. PATENT DOCUMENTS

2013/0030232 A1* 1/2013 Yanagawa ............... C10G 47/16
585/476
2016/0121313 A1* 5/2016 Zhang .................... B01J 35/108
208/111.3

FOREIGN PATENT DOCUMENTS

| KR | 1020090009165 | 1/2009 |
| KR | 1020120042059 | 5/2012 |
| KR | 1020160029972 | 3/2016 |
| KR | 1020160069273 | 6/2016 |

* cited by examiner

HYDROCRACKING CATALYST FOR PREPARING LIGHT AROMATIC HYDROCARBON, METHOD FOR PREPARING SAME AND METHOD FOR PREPARING LIGHT AROMATIC HYDROCARBON BY USING SAME

TECHNICAL FIELD

The present disclosure relates to a hydrocracking catalyst for preparing a light aromatic hydrocarbon, a method for preparing the same and a method for preparing a light aromatic hydrocarbon by using the same. More particularly, it relates to a technology of preparing a hydrocracking catalyst for preparing a light aromatic hydrocarbon from polycyclic aromatic hydrocarbons contained in byproducts of oil refining and petrochemical processes and preparing a $C_6$-$C_9$ light aromatic hydrocarbon by using the same.

BACKGROUND ART

Among the byproducts of oil refining and petrochemical processes, light cycle oil (LCO) of the fluid catalytic cracking (FCC) process, $C_{10}$+ heavy aromatics of the para-xylene process and pyrolysis fuel oil (PFO) of the naphtha cracking center (NCC) process have high polycyclic aromatic hydrocarbon (PAH) contents. Typically, they are rich in naphthalene and alkylnaphthalene.

Although these byproducts have high contents of oil components corresponding to the boiling points of light fuel oils (e.g., diesel), the quantity that may be mixed with light fuel oils is very limited due to high aromatic content and low cetane rating. Therefore, most of these byproducts are used for viscosity control of low-value heavy fuel oils or consumed as process fuel oils. However, since the demand on heavy fuel oils is decreasing rapidly, the economics of those processes can be improved significantly if it is possible to convert the low-value byproducts from oil refining and petrochemical processes, which have high contents of naphthalene and alkylnaphthalene, into light fuel oils (e.g., diesel) with high cetane rating or $C_6$-$C_9$ light aromatic hydrocarbons containing BTX (benzene, toluene and xylene) and $C_9$ aromatics (mainly trimethylbenzenes). The $C_9$ aromatics (mainly trimethylbenzenes) can be used as the main source of xylene because a technology of converting them to xylenes through transalkylation with toluene is disclosed as shown in Scheme 1.

[Scheme 1]

Toluene + Trimethylbenzenes ($C_9$ Aro.) → 2 Xylenes

For example, as shown in Scheme 2, naphthalene may be converted into high-value light aromatic hydrocarbons containing BTX and $C_9$ aromatics by selectively hydrogenating only one benzene ring of the two benzene rings of naphthalene by adding hydrogen in the presence of a catalyst, thereby converting into tetralin having a naphthene ring (reaction path 1), and consecutively hydrocracking the naphthene ring of tetralin (reaction path 2).

[Scheme 2]

Naphthalene → Tetralin → BTX + $C_9$ Aro + LPG Naphtha

Decalin → LPG, Naphtha

The reaction paths 1 and 1' are reversible reactions determined by thermodynamic equilibrium and are activated by metal catalysts. The hydrogenation whereby tetralin is produced from naphthalene is a strongly exothermic reaction in which the total number of moles is decreased. As the pressure is higher and as the reaction temperature is lower, the conversion rate of naphthalene into tetralin is higher and the yield of tetralin is higher. On the contrary, if the reaction temperature is high and the hydrogen pressure is low, the dehydrogenation reaction whereby tetralin is converted again to naphthalene becomes dominant, leading to a decreased conversion rate of naphthalene and a low yield of tetralin. The hydrogenation reaction whereby decalin is produced from tetralin also becomes dominant as the pressure is higher and as the temperature is lower.

Because the hydrocracking reaction is performed generally at high temperature and pressure, tetralin can be converted back to naphthalene through the dehydrogenation reaction (reverse reaction of the reaction path 1). In this case, the yield of light aromatic hydrocarbons containing BTX and $C_9$ aromatics is decreased. In addition, if the benzene ring of tetralin is hydrogenated and decalin is produced in large quantities (reaction path 1') due to the excessively high hydrogenation activity of the hydrocracking catalyst, the decalin is broken down into LPG and naphtha through hydrocracking reaction (reaction path 2'). As a result, the final yield of light aromatic hydrocarbons containing BTX and $C_9$ aromatics is decreased and hydrogen consumption is increased.

Therefore, in order to maximize the yield of high-value light aromatic hydrocarbons containing BTX and $C_9$ aromatics, reconversion of tetralin to naphthalene (reverse reaction of the reaction path 1) and hydrogenation of tetralin to decalin (reaction path 1') should be suppressed during the hydrocracking of tetralin. For this, a hydrocracking catalyst which maximizes the yield of light aromatic hydrocarbons containing BTX and $C_9$ aromatics by adequately controlling the hydrogenation performance of the hydrocracking catalyst, thereby minimizing the production of LPG and naphtha, is necessary.

However, when general hydrocracking catalysts are used, for example, in the hydrocracking reaction of tetralin, various $C_8$-$C_{11}$+ alkylbenzenes (ethylbenzene, propylbenzene, ethyltoluene, butylbenzene, methylpropylbenzene, ethylxylene, etc.) are produced in high yield along with the high-value light aromatic hydrocarbons containing BTX and $C_9$ aromatics (trimethylbenzenes; 1,2,4-trimethylbenzene, 1,2,5-trimethylbenzene and 1,3,5-trimethylbenzene). Therefore, as described above, development of a new catalyst for preparing high-value light aromatic hydrocarbons containing BTX and $C_9$ aromatics in high concentration is necessary through adequate control of the hydrogenation activity of the hydrocracking catalyst and adequate control of the cracking activity of zeolite such that various $C_8$-$C_{11}$+ alkylbenzenes can be converted into light aromatic hydrocarbons rich in BTX and $C_9$ aromatics.

The inventors of the present disclosure have noted that $C_6$-$C_9$ light aromatic hydrocarbons can be prepared from polycyclic aromatic hydrocarbon by using such a hydrocracking catalyst for preparing a light aromatic hydrocarbon and have completed the present disclosure.

DISCLOSURE

Technical Problem

The present disclosure has been made in consideration of the above-described problems and is directed to providing a hydrocracking catalyst for preparing a $C_6$-$C_9$ light aromatic hydrocarbon having increased contents of BTX and $C_9$ aromatics from polycyclic aromatic hydrocarbons contained in the byproducts of oil refining and petrochemical processes, a method for preparing the same and a method for preparing a $C_6$-$C_9$ light aromatic hydrocarbon by using the same.

Technical Solution

An aspect of the present disclosure relates to a hydrocracking catalyst for preparing a $C_6$-$C_9$ light aromatic hydrocarbon, which contains: (i) a composite zeolite of zeolite beta and zeolite ZSM-5; (ii) a group VIII metal; and (iii) a group VIB metal.

According to an exemplary embodiment of the present disclosure, the hydrocracking catalyst may further contain pseudoboehmite.

According to another exemplary embodiment of the present disclosure, the group VIII metal may be one or more selected from Ni and Co, and the group VIB metal may be one or more selected from Mo and W.

According to another exemplary embodiment of the present disclosure, the group VIII metal and the group VIB metal may be in the form of sulfides.

According to another exemplary embodiment of the present disclosure, the content of the composite zeolite may be 50-95 wt % based on the total weight of the hydrocracking catalyst.

According to another exemplary embodiment of the present disclosure, the content of the zeolite ZSM-5 may be 5-50 wt % based on the total weight of the composite zeolite.

According to another exemplary embodiment of the present disclosure, the composite zeolite may contain $SiO_2$ and $Al_2O_3$ at a molar ratio of 10-100:1.

According to another exemplary embodiment of the present disclosure, the contents of the group VIII metal and the group VIB metal may be 2-6 wt % and 5-25 wt %, respectively, based on the total weight of the hydrocracking catalyst.

Another aspect of the present disclosure relates to a method for preparing a hydrocracking catalyst for preparing a $C_6$-$C_9$ light aromatic hydrocarbon, including: (a) a step of preparing an aqueous metal precursor solution by dissolving group VIII and group VIB metal precursors in distilled water; (b) a step of impregnating the aqueous metal precursor solution obtained in the step (a) into a composite zeolite of zeolite beta and zeolite ZSM-5; and (c) a step of obtaining a composite zeolite-based catalyst containing group VIII and group VIB metals together by drying the composite zeolite obtained in the step (b) and then sintering the same in an oven under oxygen flow.

Another aspect of the present disclosure relates to a method for preparing a $C_6$-$C_9$ light aromatic hydrocarbon by using the hydrocracking catalyst according to the present disclosure, which includes: (1) a step of drying the hydrocracking catalyst in a reactor; (2) a step of raising the temperature of the reactor to 400-500° C., controlling pressure to 400-1500 psig and sulfurizing the hydrocracking catalyst under hydrogen-containing gas flow; (3) a step of lowering the temperature of the reactor to 120° C., controlling pressure to 500-1600 psig and controlling hydrogen flow rate to 40-100 cc/min-g-cat; (4) a step of flowing a polycyclic aromatic hydrocarbon at a flow rate of 0.03-3.3 cc/min-g-cat; and (5) a step of conducting reaction by raising the temperature of the reactor to 350-450° C. and then recovering a liquid reaction product using a gas-liquid separator.

According to an exemplary embodiment of the present disclosure, the polycyclic aromatic hydrocarbon may include one or more $C_{10}$ aromatic hydrocarbon selected from tetralin and naphthalene and one or more $C_{11}$ aromatic hydrocarbon selected from methyltetralin and methylnaphthalene.

According to another exemplary embodiment of the present disclosure, the sum of the contents of naphthalene and methylnaphthalene of the polycyclic aromatic hydrocarbon may be 0.05-30 wt % based on the total weight of the polycyclic aromatic hydrocarbon.

Advantageous Effects

According to the present disclosure, a hydrocracking catalyst for preparing a $C_6$-$C_9$ light aromatic hydrocarbons having increased contents of BTX and $C_9$ aromatics from polycyclic aromatic hydrocarbons contained in byproducts of oil refining and petrochemical processes can be prepared and, through this, a $C_6$-$C_9$ light aromatic hydrocarbon having increased contents of BTX and $C_9$ aromatics can be produced with high yield.

BEST MODE

Hereinafter, various aspects and exemplary embodiments of the present disclosure are described in more detail.

In the present disclosure "hydrocracking of a polycyclic aromatic hydrocarbon" refers to adding hydrogen to a reactant including a polycyclic aromatic hydrocarbon in the presence of a catalyst and hydrocracking the produced aromatic compound having a naphthene ring. To explain an example wherein the polycyclic aromatic hydrocarbon is naphthalene, it may be defined as a reaction whereby, as shown in Scheme 3, only one benzene ring of the two benzene rings of naphthalene is selectively hydrogenated by adding hydrogen to the naphthalene in the presence of a catalyst, thereby producing tetralin, and the naphthene ring of the tetralin is consecutively opened and broken down by hydrocracking to finally give light aromatic hydrocarbons including BTX.

[Scheme 3]

The existing technologies of converting a polycyclic aromatic hydrocarbon having two or more benzene rings, such as naphthalene and alkylnaphthalene, included in the byproducts of oil refining and petrochemical processes to high-value light aromatic hydrocarbons including BTX by using a hydrocracking catalyst have the problem that the final BTX yield is not high because, in addition to BTX, ethylbenzene (EB) and $C_9$-$C_{10}$ alkylbenzenes having one aromatic ring are produced with high yield. Because the hydrocracking catalyst according to the present disclosure has a superior activity of converting the alkylbenzenes other than BTX, which are produced with high yield, into BTX, it can solve the problem of low final BTX yield. In particular, because the hydrocracking catalyst according to the present disclosure suppresses the reconversion of tetralin, with only one benzene ring of the two benzene rings of bicyclic aromatic hydrocarbons, e.g., naphthalene, rich in polycyclic aromatic hydrocarbons selectively hydrogenated, into naphthalene and the hydrogenation of tetralin to decalin (see Scheme 2), light aromatic hydrocarbons including BTX can be obtained with high yield.

The byproducts of oil refining and petrochemical processes include light cycle oil (LCO) of the fluid catalytic cracking (FCC) process, $C_{10}$+ heavy aromatics of the para-xylene process, pyrolysis fuel oil (PFO) of the naphtha cracking center (NCC) process, etc. These byproducts are rich in bicyclic aromatic hydrocarbons such as naphthalene and alkylnaphthalene and contain all hydrocarbons including polycyclic aromatic hydrocarbons. The light aromatic hydrocarbons are $C_6$-$C_9$ hydrocarbons including BTX (benzene, toluene and xylene) and alkyl-substituted benzenes.

An aspect of the present disclosure relates to a hydrocracking catalyst for preparing a $C_6$-$C_9$ light aromatic hydrocarbon, which contains: (i) a composite zeolite of zeolite beta having a pore size of 12 MR (membered ring) and zeolite ZSM-5 having a pore size of 10 MR; (ii) a group VIII metal; and a (iii) group VIB metal. The hydrocracking catalyst may further contain pseudoboehmite as a binder.

Figure 1:
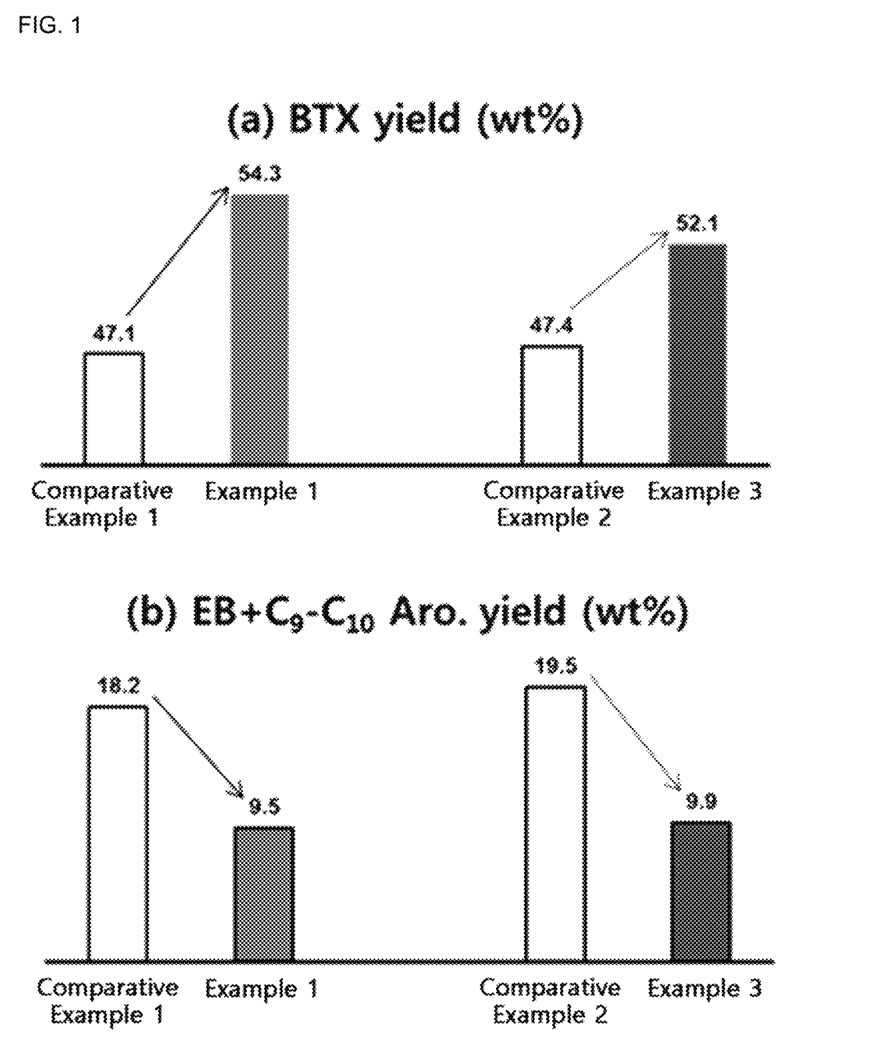
FIG. 1 shows (a) BTX yield (wt %) and (b) the yield of EB+$C_9$-$C_{10}$ aromatics (wt %) in hydrocracking of tetralin by using hydrocracking catalysts according to exemplary embodiments of the present disclosure [reaction temperature 425° C.].
Figure 2:
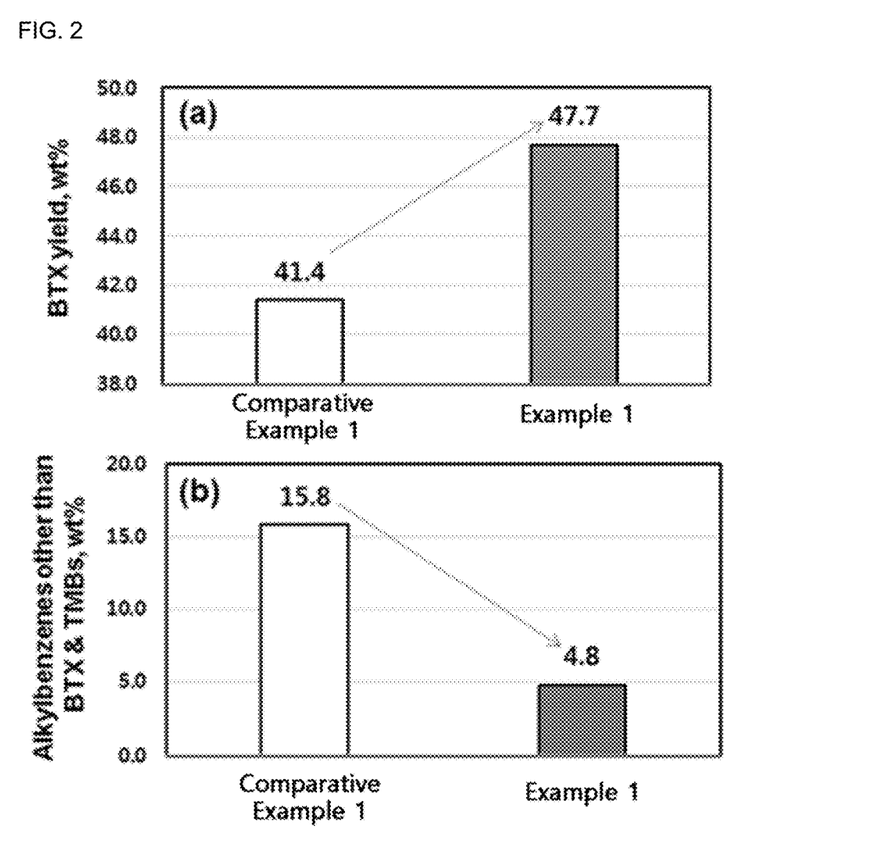
FIG. 2 shows (a) BTX yield and (b) the yield of alkylbenzenes other than BTX and trimethylbenzenes (TMBs) in hydrocracking of hydrogenated $C_{10}$+ heavy aromatics of the para-xylene process by using hydrocracking catalysts according to exemplary embodiments of the present disclosure, conducted to further confirm the performance of the hydrocracking catalysts according to the exemplary embodiments in the actual process [reaction temperature 425° C.].

In particular, the hydrocracking catalyst according to the present disclosure provides an effect of increasing the yield of BTX significantly, by using a composite zeolite of zeolite beta and zeolite ZSM-5 having a smaller pore size, rather than zeolite beta alone, as a support, because alkylbenzenes ($C_5$-$C_{10}$ alkylbenzenes including ethylbenzene, ethyltoluene, propylbenzene, butylbenzene, tetramethylbenzene, etc.) other than BTX and trimethylbenzenes are converted into BTX through dealkylation (FIG. 1 and FIG. 2).

According to an exemplary embodiment of the present disclosure, the group VIII metal may be one or more selected from Ni and Co, and the group VIB metal may be one or more selected from Mo and W. Specifically, the group VIII metal and the group VIB metal may be in the form of sulfides.

According to an exemplary embodiment of the present disclosure, the content of the composite zeolite may be 50-95 wt % based on the total weight of the hydrocracking catalyst. The conversion rate of tetralin is decreased significantly if the content is outside the above range.

According to another exemplary embodiment of the present disclosure, the content of the zeolite ZSM-5 may be 5-50 wt % based on the total weight of the composite zeolite.

If the content of the zeolite ZSM-5 is below 5 wt %, the improvement in total BTX yield is limited because the conversion activity of alkylbenzenes other than BTX into BTX is low. And, if the ZSM-5 content exceeds 50 wt %, the yield of gas products which are gas at room temperature, such as LPG, is increased and the yield of liquid products is decreased due to excessive cracking. As a result, the final BTX yield is decreased and hydrogen consumption is increased. If the ZSM-5 content is outside the above range, the yield of BTX is decreased and the yield of alkylbenzenes other than BTX is increased.

According to another exemplary embodiment of the present disclosure, the composite zeolite may contain $SiO_2$ and $Al_2O_3$ at a molar ratio of 10-100:1. If the molar ratio is below the lower limit, there are problems that the production of gas (LPG) and naphtha is increased due to excessive cracking because of high acidity of the zeolite, the yield of light aromatic hydrocarbons including BTX is decreased, and hydrogen consumption is increased. On the other hand, if the molar ratio exceeds the upper limit, high reaction temperature is required due to low acidity of the zeolite. As a result, there are problems that the reverse reaction of the reaction path 1 of Scheme 2 (reconversion of tetralin into naphthalene through dehydrogenation) is increased and the life span of the catalyst is reduced due to accelerated coke deposition, etc.

According to another exemplary embodiment of the present disclosure, the contents of the group VIII metal and the group VIB metal may be 2-6 wt % and 5-25 wt %, respectively, based on the total weight of the hydrocracking catalyst.

If the contents of the metals supported on the composite zeolite are below the lower limits, hydrogenation performance is reduced due to the decrease in the number of hydrogenation active sites of the catalyst. As a result, there are problems that tetralin is reconverted into naphthalene through dehydrogenation, the BTX content in liquid products is low due to increased production of $C_9+$ heavy aromatics and the stability of the hydrocracking catalyst is decreased due to coke deposition, etc. And, if the contents exceed the upper limits, there are problems that, due to excessively high hydrogenation activity of the catalyst, tetralin is converted into decalin and then cracked, resulting in increased production of LPG and naphtha. As a result, there are problems that the yield of liquid products and BTX is decreased and hydrogen consumption is increased (see Scheme 2).

In addition, if the hydrogenation activity of the group VIII metal supported on the composite zeolite is excessively high, there are problems that tetralin is converted into decalin and then cracked, resulting in increased production of LPG and naphtha, which leads to the decrease in final BTX yield and the increase in hydrogen consumption. When the group VIII metal is used together with the group VIB metal, the final BTX yield may be improved as the hydrogenation activity of the group VIII metal is suppressed.

In particular, if the hydrocracking catalyst according to the present disclosure does not contain any one of the zeolite beta, the zeolite ZSM-5, the group VIII metal and the group VIB metal, the BTX selectivity in liquid products and the BTX yield are decreased remarkably.

Another aspect of the present disclosure relates to a method for preparing a hydrocracking catalyst for preparing a $C_6$-$C_9$ light aromatic hydrocarbon, which includes: (a) a step of preparing an aqueous metal precursor solution by dissolving group VIII and group VIB metal precursors in distilled water; (b) a step of impregnating the aqueous metal precursor solution obtained in the step (a) into a composite zeolite of zeolite beta and zeolite ZSM-5; and (c) a step of obtaining a composite zeolite-based catalyst containing group VIII and group VIB metals together by drying the composite zeolite obtained in the step (b) and then sintering the same in an oven under oxygen flow.

Another aspect of the present disclosure relates to a method for preparing a $C_6$-$C_9$ light aromatic hydrocarbon by using the hydrocracking catalyst according to the present disclosure, which includes: (1) a step of drying the hydrocracking catalyst in a reactor; (2) a step of raising the temperature of the reactor to 400-500° C., controlling pressure to 400-1500 psig and sulfurizing the hydrocracking catalyst under hydrogen-containing gas flow; (3) a step of lowering the temperature of the reactor to 120° C., controlling pressure to 500-1600 psig and controlling hydrogen flow rate to 40-100 cc/min-g-cat; (4) a step of flowing a polycyclic aromatic hydrocarbon at a flow rate of 0.03-3.3 cc/min-g-cat; and (5) a step of conducting reaction by raising the temperature of the reactor to 350-450° C. and then recovering a liquid reaction product using a gas-liquid separator.

In the method for preparing a light aromatic hydrocarbon, if the hydrogen partial pressure for reactants is excessively low, due to the thermodynamic equilibrium relationship of tetralin during the hydrocracking reaction, tetralin is reconverted into naphthalene and the conversion rate of tetralin is decreased, resulting in decreased yield of light aromatic hydrocarbons including BTX. On the other hand, if the hydrogen partial pressure is excessively high, due to the thermodynamic equilibrium relationship of tetralin during the hydrocracking reaction, the hydrogenation of tetralin to decalin becomes dominant. As a result, there are problems that the yield of LPG and naphtha is increased due to the hydrocracking of decalin, the yield of light aromatic hydrocarbons including BTX is decreased, and hydrogen consumption is increased.

The hydrocracking reaction of polycyclic aromatic hydrocarbons described above provides an effect of increasing the BTX content in $C_6$-$C_9$ light aromatic hydrocarbons by using reactants including one or more $C_{10}$ aromatic hydrocarbon selected from tetralin and naphthalene and one or more $C_{11}$ aromatic hydrocarbon selected from methyltetralin and methylnaphthalene. The sum of the contents of naphthalene and methylnaphthalene may be 0.05-30 wt % based on the total weight of the polycyclic aromatic hydrocarbon. It may be difficult to achieve the above-described effect outside the above range.

In another exemplary embodiment of the present disclosure, the hydrocracking reaction of polycyclic aromatic hydrocarbons provides an effect that the content of xylene among BTX can be increased when oil components with high tetralin or methyltetralin content and one or more $C_{10}$ aromatic isomer selected from 1,2,4,5-tetramethylbenzene (durene), 1,2,3,5-tetramethylbenzene (isodurene) and 1,2,3,4-tetramethylbenzene (prehnitene) are used together as reactants.

The light aromatic hydrocarbon may be one or more selected from benzene, toluene, xylene and trimethylbenzenes.

MODE FOR INVENTION

Hereinafter, preparation examples and examples according to the present disclosure will be described specifically referring to the attached drawings.

The zeolites used in the examples and comparative examples of the present disclosure are generally known in the related art. Their physical properties are described in Table 1 and the composition of a composite zeolite according to the present disclosure is given in Table 2 [BZ stands for the composite zeolite of zeolite beta and zeolite ZSM-5].

TABLE 1

| Zeolite | Beta | Mordenite | ZSM-5 |
| --- | --- | --- | --- |
| $SiO_2/Al_2O_3$ molar ratio | 75.0 | 20.0 | 30.0 |
| Specific surface area (m²/g) | 650 | 500 | 405 |

TABLE 2

| Composite zeolite | BZ-1 | BZ-2 |
| --- | --- | --- |
| Beta content, wt % | 90 | 80 |
| ZSM-5 content, wt % | 10 | 20 |

Example 1: Ni(3)-Mo(8)-S/BZ-1

A catalyst with nickel and molybdenum contents of 3 wt % and 8 wt %, respectively, was prepared by impregnating an aqueous solution wherein a nickel precursor was dissolved and an aqueous solution wherein a molybdenum precursor was dissolved into composite zeolite (BZ-1) powder obtained by mixing zeolite beta ($SiO_2/Al_2O_3$=75.0) and ZSM-5 ($SiO_2/Al_2O_3$=30.0) at a weight ratio of 90:10. Nickel nitrate hexahydrate ($Ni(NO_3)_2 \cdot 6H_2O$, hereinafter "NNH") was used as the nickel precursor and ammonium molybdate tetrahydrate ($H_{24}Mo_7N_6O_{24} \cdot 4H_2O$, hereinafter "AMT") was used as the molybdenum precursor.

After impregnating a solution prepared by dissolving NNH (0.334 g) and AMT (0.331 g) in distilled water (2.5 mL) into composite zeolite BZ-1 powder (2.0 g) dried at 80° C. in the air, the resultant was dried overnight at room temperature, and then dried overnight at 80° C. After heating at a rate of 10° C./min in the air to 150° C. and keeping the temperature for 1 hour, the temperature was raised from 150° C. to 500° C. at a rate of 5° C./min and sintering was conducted for 3 hours.

The numbers in the parentheses of Ni(3)-Mo(8)-S/BZ-1 indicate the wt % values of Ni and Mo based on the total weight of the catalyst.

Example 2: Ni(3)-Mo(8)-S/BZ-2

A catalyst was prepared in the same manner as in Example 1, except that composite zeolite (BZ-2) powder obtained by mixing zeolite beta ($SiO_2/Al_2O_3$=75.0) and ZSM-5 ($SiO_2/Al_2O_3$=30.0) at a weight ratio of 80:20 was used.

Example 3: Co(3)-Mo(8)-S/BZ-1

A catalyst was prepared in the same manner as in Example 1, except that cobalt was used as the metal component instead of nickel. Cobalt(II) nitrate hexahydrate ($Co(NO_3)_2 \cdot 6H_2O$, hereinafter "CNH", 0.333 g) was used as the precursor of cobalt and AMT (0.331 g) was used as the molybdenum precursor.

Example 4: Ni(2.7)-W(19)-S/BZ-1

A catalyst was prepared in the same manner as in Example 1, except that tungsten was used as the metal component instead of molybdenum. Nickel nitrate hexahydrate ($Ni(NO_3)_2 \cdot 6H_2O$, hereinafter "NNH") was used as the nickel precursor and ammonium metatungstate (($NH_4)_6H_2W_{12}O_{40} \cdot 5H_2O$) was used as the precursor of tungsten. The impregnated catalyst was dried overnight at room temperature, further dried overnight at 80° C., heated to 500° C. at a rate of 2.5° C./min in the air, and then sintered for 3 hours.

Comparative Example 1: Ni(3)-Mo(8)-S/Beta

A catalyst was prepared in the same manner as in Example 1, except that only zeolite beta ($SiO_2/Al_2O_3$=75.0) was used as the catalyst support.

Comparative Example 2: Co(3)-Mo(8)-S/Beta

A catalyst was prepared in the same manner as in Example 3, except that only zeolite beta ($SiO_2/Al_2O_3$=75.0) was used as the catalyst support.

Comparative Example 3: Ni(3)-Mo(8)-S/Mordenite

A catalyst was prepared in the same manner as in Example 1, except that mordenite ($SiO_2/Al_2O_3$=20.0) was used as the catalyst support.

Comparative Example 4: Ni(3)-Mo(8)-S/ZSM-5

A catalyst was prepared in the same manner as in Example 1, except that only zeolite ZSM-5 ($SiO_2/Al_2O_3$=30.0) was used as the catalyst support.

Comparative Example 5: Ni(5)-S/BZ-1

A catalyst was prepared in the same manner as in Example 1, except that only nickel was supported as the metal component such that the content of nickel was 5 wt % based on the total weight of the catalyst.

Experimental Example 1: Hydrocracking of Tetralin

Hydrocracking was conducted by using tetralin as a model reactant after drying and pretreating the catalysts obtained in Examples 1-4 and Comparative Examples 1-5 as described below. The result is shown in Tables 3-4 and FIG. 1.

The catalysts prepared according to the methods of the examples and comparative examples were processed into a size of 250-500 μm. 0.58 g of the processed catalysts were filled in a fixed-bed flow reactor and the Ni, Ni—Mo, Co—Mo and Ni—W catalysts were dried at 150° C. for 1 hour under helium flow (20 cc/min). Then, sulfurization was conducted by heating to 400° C. at a rate of 0.5° C./min and maintaining the temperature for 2 hours while flowing a sulfurization feed (mixture of toluene and 1,2,4-trimethylbenzene at a molar ratio of 1:1 containing 10 vol % of dimethyl disulfide) at a flow rate of 0.16 cc/min under 460 psi hydrogen flow (83.6 cc/min).

After the sulfurization treatment of the catalysts, the reactor temperature was lowered to 120° C. and then the reactants were flown at a flow rate of 0.034 cc/min-g-cat under 588 psig hydrogen flow at a rate of 45 cc/min-g-cat. A mixture containing 100 ppm of dimethyl sulfide in tetralin was used as the reactant and the molar ratio of hydrogen/tetralin was 8.0. The reactant flow rate was WHSV (weight hourly space velocity)=2 $h^{-1}$ based on tetralin. After increasing the reactor temperature to reaction temperature, liquid products were recovered from the lower side of a gas-liquid separator after a stead state was reached. The components of the liquid products were analyzed by GC-FID and GC/MS. The performance of the catalysts was compared by calculating the conversion rate of tetralin and the selectivity and yield of BTX in the liquid products according to Equations 1-4.

Conversion rate of tetralin (wt %)=(100−tetralin content in liquid products, wt %)/100×100 [Equation 1]

Selectivity of BTX (%)=(BTX content in liquid products, wt %)/(conversion rate of tetralin)×100 [Equation 2]

Yield of BTX (wt %)=(BTX content, wt % in in liquid products)×(yield of liquid products)/100 [Equation 3]

Yield of liquid products (wt %)=(weight of liquid products produced per unit time)/(weight of reactants injected per unit time)×100 [Equation 4]

TABLE 3

| Catalyst | Reaction temperature (° C.) | Conversion rate of tetralin (wt %) | Content of monocyclic aromatic hydrocarbons with no naphthene ring (wt %) | BTX content in liquid products (%) | Yield of liquid products (wt %) | BTX yield (wt %) |
|---|---|---|---|---|---|---|
| Example 1 | 425 | 97.6 | 89.2 | 75.4 | 72.0 | 54.3 |
| Example 1 | 450 | 99.9 | 93.3 | 83.3 | 66.4 | 55.3 |
| Example 2 | 425 | 98.8 | 87.4 | 69.4 | 73.6 | 51.1 |
| Example 2 | 450 | 99.5 | 90.0 | 76.4 | 67.7 | 51.7 |
| Example 3 | 425 | 97.5 | 85.5 | 70.3 | 74.1 | 52.1 |
| Example 3 | 450 | 99.9 | 92.2 | 82.9 | 64.9 | 53.8 |
| Example 4 | 425 | 99.8 | 92.5 | 85.1 | 56.9 | 48.4 |
| Example 4 | 450 | 99.9 | 94.3 | 88.6 | 53.7 | 47.6 |
| Comparative Example 1 | 425 | 98.6 | 86.6 | 61.9 | 76.0 | 47.0 |
| Comparative Example 1 | 450 | 99.8 | 88.2 | 66.7 | 73.7 | 49.2 |
| Comparative Example 2 | 425 | 99.3 | 83.6 | 58.4 | 81.2 | 47.4 |
| Comparative Example 2 | 450 | 99.7 | 86.0 | 62.9 | 75.1 | 47.2 |
| Comparative Example 3 | 425 | 88.6 | 64.8 | 30.9 | 92.9 | 28.7 |
| Comparative Example 3 | 450 | 94.7 | 68.7 | 42.7 | 84.4 | 36.0 |
| Comparative Example 4 | 425 | 98.1 | 94.3 | 90.3 | 53.9 | 48.7 |
| Comparative Example 4 | 450 | 99.4 | 95.0 | 91.9 | 48.3 | 44.4 |
| Comparative Example 5 | 425 | 96.8 | 57.7 | 28.1 | 81.4 | 22.9 |
| Comparative Example 5 | 450 | 99.1 | 69.8 | 45.7 | 67.6 | 30.9 |

As seen from the tetralin hydrocracking reaction results shown in Table 3, the hydrocracking catalysts according to the examples of the present disclosure (Examples 1-4), wherein Ni—Mo, Co—Mo or Ni—W was supported on the composite zeolite (BZ-1 or BZ-2) of zeolite beta and ZSM-5, showed much higher BTX yield when compared with the hydrocracking catalysts according to the comparative examples (Comparative Examples 1-2), wherein Ni—Mo or Co—Mo was supported on zeolite beta without using ZSM-5.

In addition, the hydrocracking catalyst according to Comparative Example 3, wherein Ni—Mo was supported on mordenite, showed very low contents of monocyclic aromatic hydrocarbons with no naphthene ring and BTX in the liquid products under the same reaction condition when compared with other catalysts. It is thought that, when mordenite is used as the catalyst support, the BTX yield is lower as compared to the beta zeolite having a 3-dimensional pore structure, because the diffusion resistance of reactants is large and the formation of transition intermediates between two molecules is suppressed due to the 1-dimensional pore structure with no channel interaction.

In addition, for the hydrocracking catalyst wherein Ni—Mo was supported on zeolite ZSM-5 with a small pore size of 10 MR (membered ring) (Comparative Example 4), the BTX content in the liquid products was high but the BTX yield was low as compared to Examples 1-2 due to the low yield of the liquid products (high yield of gas products such as LPG, etc.).

Among the hydrocracking catalysts of Examples 1-2 according to the present disclosure, the hydrocracking catalyst of Example 1, wherein the composite zeolite of zeolite beta and ZSM-5 mixed at a weight ratio of 90:10 was used, showed high content of monocyclic aromatic hydrocarbons with no naphthene ring and high BTX yield at high tetralin conversion rate.

In addition, when compared with Example 1 wherein Ni—Mo was supported, the hydrocracking catalyst of Comparative Example 5 wherein only Ni was supported resulted in, due to excessively high hydrogenation activity of the metal, hydrogenation of a large amount of tetralin to decalin and subsequent cracking of decalin (reaction paths 1' and 2' of Scheme 2). As a result, the final BTX yield was decreased significantly as the production of gas products such as LPG, etc. was increased and the yield of liquid products was decreased greatly.

In order to explain why the hydrocracking catalysts according to the present disclosure wherein the metals were supported on the composite zeolite of zeolite beta and ZSM-5 showed high BTX yield, the detailed distribution of the liquid products obtained by hydrocracking of tetralin on the hydrocracking catalysts of Example 1 and Comparative Example 1 was compared in Table 4.

As seen from Table 4, when the composite zeolite containing 10 wt % of ZSM-5 was used, the contents of alkylbenzenes other than BTX such as ethylbenzene (EB), $C_9$ aromatics (propylbenzene, ethyltoluene, trimethylbenzene, etc.), $C_{10}$ aromatics (butylbenzene, tetramethylbenzene, etc.), etc. in the liquid products obtained from the hydrocracking of tetralin were decreased remarkably and the content of BTX was increased as compared to when zeolite beta not mixed with ZSM-5 was used. It is thought that the addition of zeolite ZSM-5 having a smaller pore size than zeolite beta improves the yield of BTX as alkylbenzenes other than BTX (EB+$C_9$-$C_{10}$ aromatics) are converted into BTX by dealkylation. The same effect of the present disclosure was observed for all the metal components supported to prepare the hydrocracking catalysts.

TABLE 4

| Main components | Comparative Example 1 [Ni(3)-Mo(8)-S/Beta] | | Example 1 [Ni(3)-Mo(8)-S/BZ-1] | |
|---|---|---|---|---|
| | 425 | 450 | 425 | 450 |
| Tetralin | 1.4 | 0.2 | 2.4 | 0.1 |
| Nonaromatic hydrocarbons | 10.4 | 9.3 | 7.4 | 5.8 |
| Ethylbenzene | 11.3 | 8.8 | 6.5 | 4.2 |
| Benzene | 29.3 | 29.1 | 34.7 | 34.2 |
| Toluene | 24.4 | 27.3 | 30.3 | 35.6 |
| Xylene | 8.2 | 10.4 | 10.5 | 13.4 |
| $C_9$ aromatic hydrocarbons | 10.0 | 9.0 | 5.6 | 5.0 |
| Indane | 0.4 | 0.4 | 0.2 | 0.1 |
| Methylindane | 0.3 | 0.3 | 0.1 | 0.1 |
| Decalin | 0.0 | 0.0 | 0.0 | 0.0 |
| Naphthalene | 0.4 | 0.7 | 0.3 | 0.3 |
| 2-Methylnaphthalene | 0.3 | 0.6 | 0.2 | 0.2 |
| 1-Methylnaphthalene | 0.1 | 0.3 | 0.1 | 0.1 |
| Other $C_{10}$ aromatic hydrocarbons | 2.6 | 2.2 | 1.1 | 0.6 |
| Other $C_{11}$ aromatic hydrocarbons | 0.5 | 0.6 | 0.2 | 0.1 |
| Other $C_{11}$+ aromatic hydrocarbons | 0.4 | 0.8 | 0.4 | 0.2 |
| Total | 100.0 | 100.0 | 100.0 | 100.0 |

Experimental Example 2: Hydrocracking of $C_{10}$+ Heavy Aromatics of Para-Xylene Process In order to confirm the performance of the hydrocracking catalysts according to the examples of the present disclosure, hydrocracking was conducted by using $C_{10}+$ heavy aromatics actually produced from the para-xylene process as reactants, as examples of polycyclic aromatic hydrocarbons. As illustrated in Schemes 2 and 3, naphthalene, alkylnaphthalenes, etc. having two benzene rings, included in the polycyclic aromatic hydrocarbons were converted into tetralin and alkyltetralins by adding hydrogen in the presence of the catalysts and then subjected to hydrocracking. The composition of the $C_{10}+$ heavy aromatics before and after the hydrogenation is shown in Table 5. The hydrogenation treatment of the $C_{10}+$ heavy aromatics produced from the para-xylene process was performed according to the previously reported method [Korean Patent Registration Publication No. 10-1528158]. As shown in Table 5, after the hydrogenation treatment, the contents of naphthalene and methylnaphthalene were decreased greatly and, instead, the contents of tetralin and methyltetralin were increased greatly. Besides, the $C_{10}+$ heavy aromatics actually produced from the para-xylene process were rich in tetramethylbenzene ($C_{10}$ aromatic) with one benzene ring and included various components such as methylbiphenyl, dimethylbiphenyl, etc. having two or more benzene rings.

TABLE 5

| Main components | Before hydrogenation treatment ($C_{10}+$ heavy aromatics) | After hydrogenation treatment |
|---|---|---|
| Nonaromatic hydrocarbons | — | 0.0 |
| Ethylbenzene | — | 0.2 |
| Benzene | — | 0.0 |
| Toluene | — | 0.1 |
| Xylene | — | 0.4 |
| C9 aromatic hydrocarbons | 0.1 | 2.0 |
| 1,2,4,5-Tetramethylbenzene | 2.2 | 2.1 |
| 1,2,3,5-Tetramethylbenzene | 4.3 | 4.2 |
| 1,2,3,4-Tetramethylbenzene | 9.6 | 9.9 |
| Methylindane | 2.4 | 1.2 |
| Tetralin | 0.2 | 13.2 |
| Methyltetralin | 0.6 | 10.2 |
| Naphthalene | 9.8 | 0.1 |
| 2-Methylnaphthalene | 8.5 | 0.9 |
| 1-Methylnaphthalene | 4.1 | 0.1 |
| Other $C_{10}$ aromatic hydrocarbons | 8.4 | 8.6 |
| Other $C_{11}$ aromatic hydrocarbons | 11.6 | 22.1 |
| Other $C_{11}+$ aromatic hydrocarbons | 38.2 | 24.6 |
| Total | 100.0 | 100.0 |

In Experimental Example 2, hydrocracking was conducted under the same condition as in Experimental Example 1, except that the reactants of hydrocracking were changed from the model tetralin to the hydrogenation-treated $C_{10}+$ heavy aromatics of the para-xylene process. The results of hydrocracking the hydrogenation-treated $C_{10}+$ heavy aromatics of the para-xylene process by using the hydrocracking catalyst according to Comparative Example 1 (Ni(3)-Mo(8)-S/Beta) and the hydrocracking catalyst according to Example 1 (Ni(3)-Mo(8)-S/BZ-1) at a reaction temperature of 425° C. are compared in Table 6 and FIG. 2 [alkylbenzenes other than (BTX+TMBs (trimethylbenzenes))=$C_8$-$C_{10}$ alkylbenzenes including ethylbenzene, ethyltoluene, propylbenzene, butylbenzene, tetramethylbenzene, etc.].

The performance of the catalysts was calculated according to Equations 5-8.

Conversion rate of tetralin (wt %)=(tetralin content in reactants, wt %−tetralin content in liquid products, wt %)/(tetralin content in reactants, wt %)×100   [Equation 5]

Conversion rate of methyltetralin (wt %)=(methyltetralin content in reactants, wt %−methyltetralin content in liquid products, wt %)/(methyltetralin content in reactants, wt %)×100   [Equation 6]

Conversion rate of tetralins (wt %)=(content of tetralins in reactants, wt %−content of tetralins in liquid products, wt %)/(content of tetralins in reactants, wt %)×100   [Equation 7]

Yield of BTX (wt %)=(BTX content in liquid products, wt %)×(yield of liquid products)/100   [Equation 8]

TABLE 6

| Hydrocracking catalyst | | Comparative Example 1 | Example 1 |
|---|---|---|---|
| Reaction temperature (° C.) | | 425 | 425 |
| Components of reaction products (wt %) | Nonaromatic hydrocarbons | 10.7 | 7.8 |
| | Ethylbenzene | 2.9 | 1.1 |
| | Benzene | 4.0 | 7.0 |
| | Toluene | 17.2 | 27.4 |
| | Xylene | 28.0 | 34.2 |
| | Ethyltoluene | 6.5 | 2.7 |
| | 1,3,5-Trimethylbenzene | 4.9 | 4.0 |
| | 1,2,4-Trimethylbenzene | 10.8 | 10.0 |
| | 1,2,3-Trimethylbenzene | 1.6 | 1.4 |
| | 1,2,4,5-Tetramethylbenzene | 1.1 | 0.6 |
| | 1,2,3,5-Tetramethylbenzene | 1.2 | 0.8 |
| | 1,2,3,4-Tetramethylbenzene | 0.4 | 0.3 |
| | Tetralin | 0.2 | 0.1 |
| | Methyltetralin | 0.3 | 0.0 |
| | Naphthalene | 0.1 | 0.1 |
| | 2-Methyl naphthalene | 0.1 | 0.1 |
| | 1-Methyl naphthalene | 0.1 | 0.1 |
| | Other $C_9$ aromatic hydrocarbons | 0.7 | 0.2 |
| | Other $C_{10}$ aromatic hydrocarbons | 4.5 | 1.2 |
| | Other $C_{11}$ aromatic hydrocarbons | 1.3 | 0.2 |
| | Other $C_{11}+$ aromatic hydrocarbons | 3.4 | 0.7 |
| Total | | 100.0 | 100.0 |
| Conversion rate of tetralin, wt % | | 98.3 | 99.1 |
| Conversion rate of methyltetralin, wt % | | 95.1 | 99.6 |
| Conversion rate of tetralins, wt % | | 97.2 | 99.3 |
| BTX content in liquid products, wt % | | 49.3 | 68.6 |
| Content of alkylbenzenes other than (BTX + trimethylbenzenes (TMBs)) in liquid products, wt % | | 18.8 | 6.9 |
| Content of (BTX + $C_9$ aromatic) in liquid products, wt % | | 73.9 | 86.9 |
| Yield of liquid product, wt % | | 84.1 | 69.5 |
| BTX yield, wt % | | 41.4 | 47.7 |
| Yield of (BTX + $C_9$ aromatics), wt % | | 62.1 | 60.4 |

According to Experimental Example 2, the conversion rate of tetralin, methyltetralin and tetramethylbenzenes (1,2,4,5-tetramethylbenzene, 1,2,3,5-tetramethylbenzene and 1,2,3,4-tetramethylbenzene) included in the hydrogenation-treated $C_{10}+$ heavy aromatics was very high for the hydrocracking catalyst according to Example 1 (Table 6). In addition, the conversion rate of other $C_{10}$-$C_{11}+$ heavy aromatics was also very high. In particular, when the hydrocracking catalyst according to Example 1 was used, the final yield of BTX was improved remarkably as compared to when the hydrocracking catalyst according to Comparative Example 1 was used. That is to say, whereas the BTX yield in hydrocracking was 41.4 wt % when the hydrocracking catalyst according to Comparative Example 1 was used, the BTX yield was increased to 47.7 wt % when the hydrocracking catalyst according to Example 1 was used (Table 6). When the composite zeolite of zeolite beta and ZSM-5 was used as in the hydrocracking catalyst according to Example 1 according to the present disclosure, the contents of alkylbenzenes other than (BTX+trimethylbenzenes) such as ethylbenzene (EB), $C_9$ aromatics (propylbenzene, ethyltoluene, etc.), $C_{10}$ aromatics (butylbenzene, tetramethylbenzene, etc.), etc. are decreased greatly in the liquid products obtained from the hydrocracking of the hydrogenation-treated $C_{10}+$ heavy aromatics and the BTX yield was increased as compared to when the hydrocracking catalyst according to Comparative Example 1 with no ZSM-5 was used. It is thought that these results are attributed to the conversion of alkylbenzenes other than (BTX+trimethylbenzenes) into BTX by dealkylation when the composite zeolite of zeolite beta and ZSM-5 according to the present disclosure is used.

The $C_9$ aromatics including trimethylbenzenes (1,3,5-trimethylbenzene, 1,2,4-trimethylbenzene and 1,2,3-trimethylbenzene) from the actual para-xylene process are useful components that can be converted into xylene through disproportionation reaction with toluene as shown in Scheme 1. The yield of $C_9$ aromatics including BTX and trimethylbenzenes (BTX+$C_9$ aromatics) was comparably high in the range of 60-62 wt % when the catalysts according to Comparative Example 1 and Example 1 were used.

In addition, according to Experimental Example 2 of the present disclosure, the content of BTX in the liquid products obtained from the hydrocracking reaction of the hydrogenation-treated $C_{10}+$ heavy aromatics was in the order of xylene>toluene>>benzene, as shown in Table 6. For Example 1, the content of ethylbenzene was very low as 1.1 wt %. This result shows significant difference from the composition of the liquid products of hydrocracking using tetralin on the same hydrocracking catalyst (Example 1) (Table 4). The high content of high-value xylene and the very low content of ethylbenzene are very desirable results. It seems that the remarkable increase in the content of xylene among BTX in the hydrocracking of hydrogenation-treated $C_{10}+$ heavy aromatics compared to the hydrocracking of tetralin is the result of Scheme 4. That is to say, it is thought that the yield of xylene is increased and the yield of benzene is decreased due to transalkylation (Scheme 4) between benzene and toluene, which are obtained with high yield from hydrocracking of tetralins, and tetramethylbenzenes (1,2,4,5-tetramethylbenzene, 1,2,3,5-tetramethylbenzene and 1,2,3,4-tetramethylbenzene), which are rich in the $C_{10}+$ heavy aromatics of the actual para-xylene process. In addition, the increase in the contents of trimethylbenzenes ($C_9$ aromatic hydrocarbons), which are included in the hydrogenation-treated $C_{10}+$ heavy aromatics in trace amounts, by the hydrocracking reaction can also be explained by Scheme 4. That is to say, it is thought that the trimethylbenzenes ($C_9$ aromatic hydrocarbons) are produced by Schemes (4-1) and (4-2).

Also, according to Experimental Example 2 of the present disclosure, it can be seen that the $C_{11}$ and $C_{11}+$ aromatic hydrocarbons, which are included in considerable amounts in the reactants, are mostly converted to $C_6$-$C_9$ light aromatic hydrocarbons through the hydrocracking reaction, as can be seen from comparison of Table 5 and Table 6.

[Scheme 4]

(4-1)

Tetramethylbenzenes    Benzene    Xylenes

Toluene    Trimethylbenzenes
(4-2)

Tetramethylbenzenes    Toluene    Xylenes

Trimethylbenzenes

Therefore, according to the present disclosure, the effect of obtaining $C_6$-$C_9$ light aromatic hydrocarbons having an increased BTX content from the byproducts of oil refining and petrochemical processes, wherein polycyclic aromatic hydrocarbons such as naphthalene, alkylnaphthalenes, etc. are included, can be achieved with high yield by using a catalyst wherein a group VIII metal and a group VIB metal are supported on the composite zeolite support of zeolite beta and zeolite ZSM-5.

INDUSTRIAL APPLICABILITY

According to the present disclosure, a hydrocracking catalyst for preparing a $C_6$-$C_9$ light aromatic hydrocarbon having increased contents of BTX and $C_9$ aromatics from polycyclic aromatic hydrocarbons contained in byproducts of oil refining and petrochemical processes can be prepared and, through this, a $C_6$-$C_9$ light aromatic hydrocarbons having increased contents of BTX and $C_9$ aromatics can be produced with high yield.

The invention claimed is:
1. A method for preparing a $C_6$-$C_9$ light aromatic hydrocarbon with a hydrocracking catalyst, comprising:
(i) a composite zeolite comprising zeolite beta and zeolite ZSM-5, wherein the zeolite ZSM-5 is present in an amount of 5-20 weight % based on a total weight of the composite zeolite and wherein the weight ratio of zeolite beta and ZSM-5 in the composite zeolite is 90:10-80:20;
(ii) a group VIII metal; and
(iii) a group VIB metal;
the method comprising:
drying the hydrocracking catalyst in a reactor;
raising a temperature of the reactor to 400-500° C., controlling pressure to 400-1500 psig and sulfurizing the hydrocracking catalyst under hydrogen-containing gas flow;
lowering the temperature of the reactor to 120° C., controlling pressure to 500-1600 psig and controlling hydrogen flow rate to 40-100 cc/min·g–cat;
flowing a polycyclic aromatic hydrocarbon at a flow rate of 0.03-3.3 cc/min·g–cat; and conducting a reaction by raising the temperature of the reactor to 350-450° C., thereby producing a hydrocracking product comprising a $C_6$-$C_9$ light aromatic hydrocarbon, and then recovering a liquid reaction product using a gas-liquid separator.

2. The method for preparing a $C_6$-$C_9$ light aromatic hydrocarbons according to claim 1, wherein the polycyclic aromatic hydrocarbon comprises one or more $C_{10}$ aromatic hydrocarbon selected from tetralin and naphthalene and one or more $C_{11}$ aromatic hydrocarbon selected from methyltetralin and methylnaphthalene.

3. The method for preparing a $C_6$-$C_9$ light aromatic hydrocarbons according to claim 2, wherein a sum of contents of naphthalene and methylnaphthalene of the polycyclic aromatic hydrocarbon is 0.05-30 wt % based on a total weight of the polycyclic aromatic hydrocarbon.

4. The method according to claim 1, wherein the zeolite ZSM-5 is present in an amount of 5-10 weight % based on a total weight of the composite zeolite.

5. The method for preparing a $C_6$-$C_9$ light aromatic hydrocarbons according to claim 4, wherein the polycyclic aromatic hydrocarbon comprises one or more $C_{10}$ aromatic hydrocarbon selected from tetralin and naphthalene and one or more $C_{11}$ aromatic hydrocarbon selected from methyltetralin and methylnaphthalene.

6. The method for preparing a $C_6$-$C_9$ light aromatic hydrocarbons according to claim 4, wherein a sum of contents of naphthalene and methylnaphthalene of the polycyclic aromatic hydrocarbon is 0.05-30 wt % based on a total weight of the polycyclic aromatic hydrocarbon.

7. The method according to claim 1, wherein the zeolite ZSM-5 is present in an amount of 10-15 weight % based on a total weight of the composite zeolite.

8. The method according to claim 1, wherein the zeolite ZSM-5 is present in an amount of 15-20 weight % based on a total weight of the composite zeolite.

9. The method according to claim 1, wherein the zeolite ZSM-5 is present in an amount of 5-15 weight % based on a total weight of the composite zeolite.

10. The method according to claim 1, wherein the zeolite ZSM-5 is present in an amount of 10-20 weight % based on a total weight of the composite zeolite.

11. The method for preparing a $C_6$-$C_9$ light aromatic hydrocarbons according to claim 10, wherein the polycyclic aromatic hydrocarbon comprises one or more $C_{10}$ aromatic hydrocarbon selected from tetralin and naphthalene and one or more $C_{11}$ aromatic hydrocarbon selected from methyltetralin and methylnaphthalene.

12. The method for preparing a C6-C9 light aromatic hydrocarbons according to claim 10, wherein a sum of contents of naphthalene and methylnaphthalene of the polycyclic aromatic hydrocarbon is 0.05-30 wt ¾ based on a total weight of the polycyclic aromatic hydrocarbon.

* * * * *